(12) United States Patent
Chen et al.

(10) Patent No.: US 7,955,263 B2
(45) Date of Patent: Jun. 7, 2011

(54) NON-INVASIVE POSITIONING SYSTEM FOR LOCATING THE FOCUS OF HIGH-INTENSITY FOCUSED ULTRASOUND

(75) Inventors: Chiung-Nien Chen, Taipei (TW);
Po-Huang Lee, Taipei (TW);
Wen-Shiang Chen, Taipei (TW);
Ming-Chih Ho, Taipei (TW);
Chih-Ching Wu, Taipei (TW)

(73) Assignee: National Taiwan University, Taipei (TW)

( * ) Notice: Subject to any disclaimer, the term of this patent is extended or adjusted under 35 U.S.C. 154(b) by 1145 days.

(21) Appl. No.: 11/707,109

(22) Filed: Feb. 16, 2007

(65) Prior Publication Data
US 2007/0232912 A1    Oct. 4, 2007

(30) Foreign Application Priority Data

Feb. 20, 2006    (TW) .............................. 95105619 A (51) Int. Cl.
*A61B 8/00*    (2006.01)

(52) U.S. Cl. ....................................................... 600/439
(58) Field of Classification Search .................... 600/439
See application file for complete search history.

(56) References Cited

U.S. PATENT DOCUMENTS

2005/0203399 A1*    9/2005   Vaezy et al. ................. 600/439
* cited by examiner

*Primary Examiner* — Long V Le
*Assistant Examiner* — Saurel J Selkin
(74) *Attorney, Agent, or Firm* — Birch, Stewart, Kolasch & Birch, LLP (57) ABSTRACT

A non-invasive positioning system for determining the focus location of a HIFU device comprises a diagnostic ultrasound and the HIFU for ablating and removing tumor tissue. The imaging plane of the diagnostic ultrasound probe and the geometrical axis of a probe of the HIFU define an inclining angle during operation. When the imaging plane of the diagnostic ultrasound intersected to the focus of the HIFU transducer, a maximal convergent interference signals was obtained, so as to position the HIFU focus within tumors for precise ablation.

4 Claims, 7 Drawing Sheets
(5 of 7 Drawing Sheet(s) Filed in Color)

NON-INVASIVE POSITIONING SYSTEM FOR LOCATING THE FOCUS OF HIGH-INTENSITY FOCUSED ULTRASOUND

BACKGROUND OF THE INVENTION

1. Field of the Invention

The present invention relates to a positioning system for locating the focus of a high-intensity focused ultrasound (HIFU) device in vivo, and more particularly to a non-invasive positioning system combining a diagnostic and a HIFU systems while being used for positioning the focus of the HIFU device in vivo.

2. The Prior Arts

Cancer has been a major threat for humans for years. Many patients are diagnosed with various tumors in their bodies every year, but frequently it's too late to resect the tumor tissues via surgical operation due to metastasis. Meanwhile, conventional chemical or radioactive therapies have limited therapeutic effects, especially for hepatoma and pancreatic cancers in the abdominal cavity. Furthermore, patients having recurrent or metastatic tumors are usually not good candidates for repeated surgical operations or chemical therapies. Patients cannot receive repeated radiotherapy due to the safety concern of radiation accumulation. Moreover, for certain benign tumors (e.g., fibroid in the uterus), space-occupying brain tumors, or metastasis, patients hope to be treated non-invasively.

Recently, the invention of high-intensity focused ultrasound for cancer therapy provides a non-invasive and effective way for tumor therapy. HIFU can induce coagulative necrosis on tumor tissues by thermal ablation, and then the necrotic tumor tissues are absorbed so as to efficiently decrease the tumor volume. For instance, the uterine fibroid, which causes over-hemorrhaging and affects the normal uterine function, can be efficiently treated by HIFU therapy without any surgical operation. Even though the uterine fibroid regenerates later, HIFU therapy can be used to treat the regenerated tissues again.

HIFU can be used to treat and remove tumor tissues in vivo in a non-invasive manner, but conventional diagnostic ultrasound provides limited images to precisely position the focus location of the HIFU device, especially when sound waves from HIFU deflect or scatter in vivo. Usually, a diagnostic ultrasound system is used to roughly position the HIFU focus on the target tumor tissues in a patient's body first. By integrating the diagnostic and HIFU transducers, the focus of HIFU is located on a pre-determined position on the obtained ultrasonic images. HIFU is then used to ablate the target region. Because the ablated regions are hyperechoic and capable of being observed by the conventional diagnostic ultrasound, it is possible to ensure if the ablated regions correspond to the locations of the tumor tissues. If the hyperechoic regions do not correspond to the locations of tumor tissues, the focus of HIFU is adjusted and the ablating procedure is repeated. However, the above method has several problems detailed in the following: (1) The ablated regions produced by HIFU generate denatured tissues which cannot be distinguished on images of the conventional diagnostic ultrasound; (2) The hyperechoes might represent an overheating situation which may damage the surrounding normal tissues; (3) Permanent damage has already been produced if observable changes, e.g., hyperechoes, on ultrasonic images were produced; (4) Since the HIFU produces interference on the diagnostic ultrasound images, HIFU cannot be used for real-time monitoring the ablation process and results. This situation is especially problematic when the tumor tissues shift during ablation (e.g., the tumor tissues adjacent to the lungs may shift due to breathing), or only a small volume is required to be precisely removed (e.g., a small volume of brain tissue); and (5) If bubbles are generated during ablations, HIFU can not penetrate the bubble cloud to treat the tumor tissue located beneath so as to reduce the actual therapeutic effect.

To ensure if the ablated regions align with the locations of the tumor tissues, magnetic resonance imaging (MRI) technology was developed to precisely position the locations of tumor tissues in a 3-dimensional manner using MRI followed by ablation using HIFU. Although the MRI technology can precisely position the locations of tumor tissues in a patient's body, the MRI scan is too expensive, occupies more operating space, and may not monitor the ablation region in real-time.

Therefore, it is important to develop a non-invasive positioning method using diagnostic ultrasound for the focus of HIFU. The non-invasive positioning system can be used to precisely position the ablated regions in real-time while efficiently preventing damage to the surrounding normal tissues.

SUMMARY OF THE INVENTION

To overcome the problems as described above, a primary objective of the present invention is to provide a non-invasive positioning system for focus localization of a HIFU device, which can detect in real-time so that the HIFU can precisely ablate tumor tissues while efficiently preventing damage to surrounding normal tissues.

To achieve the above objective, the non-invasive positioning system for focus localization of HIFU according to a preferred embodiment of the present invention comprises:
(1) a diagnostic ultrasound device used for primarily detecting and estimating a location of a tumor tissue in vivo;
(2) a HIFU device used for ablating the tumor tissue; and
(3) an image display device used for showing a detection signal generated by the diagnostic ultrasound device;
wherein when using the non-invasive positioning system to position the focus of the HIFU device, a geometric axis of the diagnostic ultrasound probe is substantially non-parallel with a geometric axis of a probe of the HIFU device, and an inclining angle between the geometric axes of the probes of the diagnostic ultrasound device and the geometric axes of the probes of the HIFU device preferably has a range from 85 degrees to 160 degrees, wherein the diagnostic ultrasound device has an imaging plane which is substantially intersected to the focus on the geometric axis of the probe of the HIFU device.

A secondary objective of the present invention is to provide a non-invasive positioning method for focus localization of a HIFU device in vivo, wherein the non-invasive positioning method can precisely detect ablating points of tumor tissues in real-time so that the HIFU device can precisely remove tumor tissues. The non-invasive positioning method for focus localization of HIFU according to a preferred embodiment of the present invention comprises steps of:
(i) primarily scanning and estimating the location of a tumor tissue in vivo by using a diagnostic ultrasound device;
(ii) operating the HIFU device at a relatively low power to align the ultrasound provided thereby with the location of the tumor tissue detected in step (i);
(iii) adjusting the scanning angle of the diagnostic ultrasound device until maximal interference convergence is observed on the ultrasounds intersection provided respectively from the diagnostic ultrasound device and the HIFU device, wherein the inclining angle defined between geometric axes of the respective probes of the diagnostic ultrasound device and the HIFU device has a range from 85 to 160 degrees; and (iv) determining the focus of the HIFU device by locating where the maximal interference convergence is observed using the diagnostic ultrasound device.

As described above, the focus location of the HIFU device will be adjusted to overlap with the location of the tumor tissue in vivo by the non-invasive positioning method of the present invention, and then one could project the HIFU device with a relatively high power to the location of the tumor tissue for ablating and removing tumor tissue.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The structure and the technical means adopted by the present invention to achieve the above and other objects can be best understood by referring to the following detailed description of the preferred embodiments and the accompanying drawings, wherein

FIG. 4B shows the image of intensive interference signals under the B mode; and FIG. 4C shows the image of intensive interference signals under the Doppler mode);

DETAILED DESCRIPTION OF THE PREFERRED EMBODIMENTS

Figure 1:
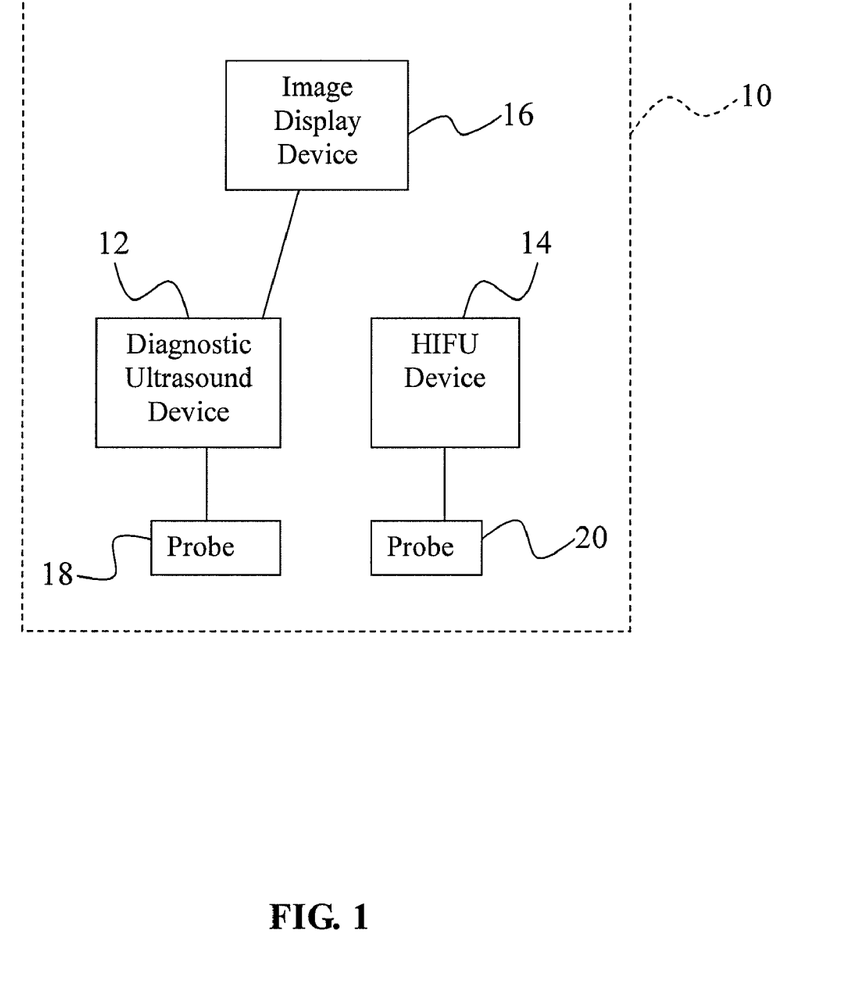
FIG. 1 is a schematic view of a non-invasive positioning system according to a preferred embodiment of the present invention.

Referring now to FIG. 1, a schematic view of a non-invasive positioning system for the focus location of HIFU according to a preferred embodiment of the present invention is illustrated. As shown, the non-invasive positioning system of the present invention designated by numeral 10 comprises a diagnostic ultrasound device 12 used for primarily detecting at least one location of at least one tumor tissue in vivo, a HIFU device 14 used for ablating the tumor tissue, and an image display device 16 used for showing at least one detection signal generated by the diagnostic ultrasound device 12. The diagnostic ultrasound device 12 is provided with a probe 18 adapted to emit at least one diagnostic ultrasound and receive at least one echo of the diagnostic ultrasound. The diagnostic ultrasound device 12 can be selected from any traditional ultrasound emitter and receiver, without limitation, for locating a detected object, such as the tumor tissue.

Referring still to FIG. 1, the HIFU device 14 according to the preferred embodiment of the present invention is provided with a probe 20 adapted to emit at least one HIFU with a relatively high power for ablating the tumor tissue. The HIFU device 14 can be selected from any HIFU system, without limitation, for ablating a treated object, such as the tumor tissue.

Referring still to FIG. 1, the image display device 16 according to the preferred embodiment of the present invention is connected to the diagnostic ultrasound device 12 for showing at least one detected signal generated by the diagnostic ultrasound device 12. The image display device 16 can be selected from any traditional image display, without limitation, for showing detected signals generated by the traditional ultrasound devices.

Figure 2:
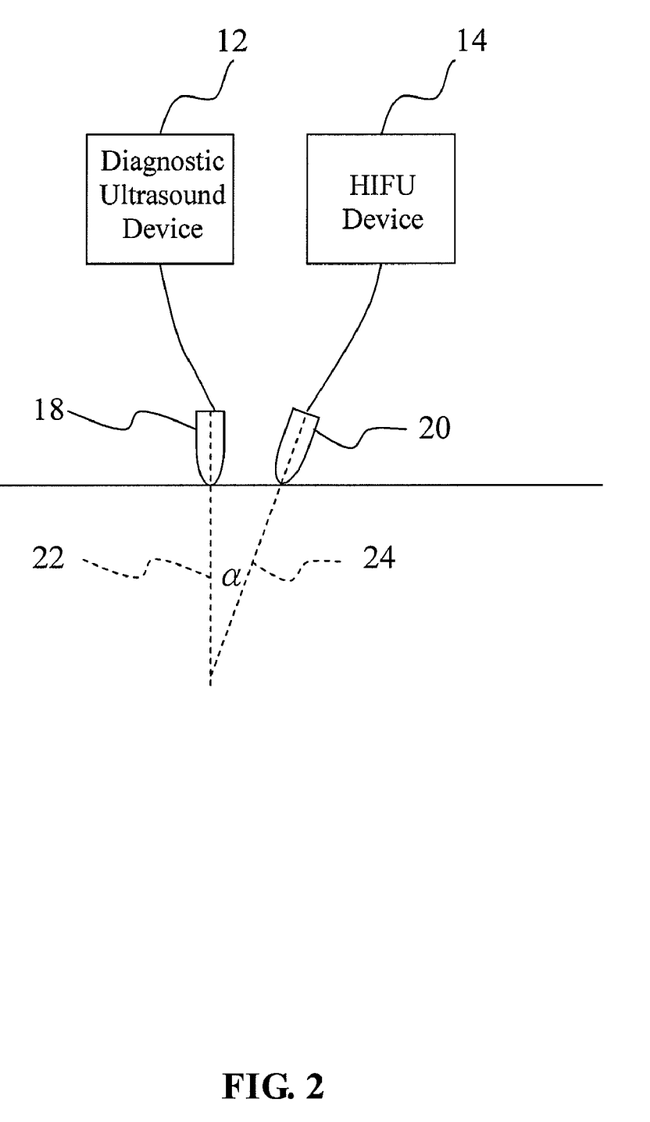
FIG. 2 is a schematic view of the non-invasive positioning system according to a preferred embodiment of the present invention in using manner.

Referring now to FIG. 2, when the non-invasive positioning system 10 of the present invention is used to position at least one location of the focus of the HIFU device 14, the probe 18 of the diagnostic ultrasound device 12 shifts along a skin surface (unlabeled) of a patient while emitting at least one diagnostic ultrasound and receiving at least one echo of the diagnostic ultrasound for primarily detecting at least one location of at least one tumor tissue within the patient. And then, the HIFU device 14 is actuated to generate ultrasonic waves with a relatively low power so that a geometric axis 24 of the probe 20 thereof is substantially intersected to an observation plane (not shown) of the diagnostic ultrasound device 12 in a non-parallel manner as shown in FIG. 2. The relatively low power of HIFU as described above means a intensity of ultrasound power is not intensive enough to burn any tissue within the patient, and the ultrasound power value of the diagnostic ultrasound device 12 preferably has a range from 0.01 W to 5 W. To intersect the geometric axis 24 of the probe 20 to the observation plane (unlabeled) of the diagnostic ultrasound device 12, the geometric axis 24 of the probe 20 is substantially non-parallel with the geometric axis 22 of the probe 18 so as to define an inclining angle α. For convenient operation, the inclining angle α preferably has a range from 85 degrees to 160 degrees. Thus, the image display device 16 can show that an intensive interference signal is generated at an intersected point which the observation plane of the diagnostic ultrasound device 12 is substantially intersected to the focus on the geometric axis 24 of the probe 20 of the HIFU device 14 (the intensive interference signal is greater than the background noise signal). Where the intensive interference signal is generated is advantageous to efficiently position the focus location of the HIFU device 14, i.e. a predetermined ablating point. After ensuring the predetermined ablating point, comparing the predetermined ablating point detected by the HIFU device 14 to the actual location of the tumor tissue within the patient detected by the diagnostic ultrasound device 12. If the predetermined ablating point is not the same as the actual location of the tumor tissue, the HIFU device 14 will be adjusted until the focus location (i.e. the predetermined ablating point) thereof is the same as the actual location of the tumor tissue, which should be burned. After this, the HIFU device 14 will be adjusted to output a HIFU with a relatively high power, which preferably is an ultrasound power value having a range from 30 W to 60 W for precisely ablating the tumor tissue within the patient. As described above, the geometric axis 24 of the HIFU device 14 is a supposed line extending outwards from the probe 20 and parallel to an output direction of the HIFU waves generated by the HIFU device 14. Furthermore, the observation plane of the diagnostic ultrasound device 12 is a supposed plane extending outwards from the probe 18 and parallel to an outputting direction of the diagnostic ultrasound generated by the diagnostic ultrasound device 12, and the observation plane thereof is intersected to the geometric axis 24 of the HIFU device 14 to define the inclining angle α. The observation plane comprises the geometric axis 24 of the HIFU device 14.

As described above, the non-invasive positioning system 10 according to the preferred embodiment of the present invention can precisely position the focus location (i.e. the predetermined ablating point) of the HIFU device 14 by using the diagnostic ultrasound device 12 and the HIFU device 14. As will be described in more detail below, the diagnostic ultrasound device 12 can be used to simultaneously position the predetermined ablating point during ablating by the HIFU device 14 to carry out real-time detection.

In another aspect, the non-invasive positioning system 10 according to the preferred embodiment of the present invention can position the actual location of the tumor tissue without using any MRI device having complicated, expensive, and space problems, the non-invasive positioning system 10 of the present invention can provide the advantages of easy operation, low cost, and real-time detection to solve the problems existing in conventional therapeutic technology.

The invention will now be further explained and illustrated by reference to the following non-limiting examples.

Example 1

According to the preferred embodiment of the present invention (as shown in FIGS. 1 and 2), the non-invasive positioning system 10 is pre-tested by using a water sink (not shown) with purified water as a medium. First, the probe 18 of the diagnostic ultrasound device 12 and the probe 20 of the HIFU device 14 of the non-invasive positioning system 10 are mounted above the water sink so that the geometric axis 22 of the probe 18 and the geometric axis 24 of the probe 20 are intersected to define the inclining angle α (from 80 degrees to 100 degrees in Example 1). Then, the diagnostic ultrasound device 12 and the HIFU device 14 are turned on respectively while the power value output of the HIFU device 14 is controlled with a relatively low power value about 0.75 W. To detect signals, the probe 18 of the diagnostic ultrasound device 12 shifts forwards and backwards parallel to the top surface of the water sink with a fixed inclining angle so that the intersection point of geometric axes 22, 24 can move along the geometric axis 24 of the probe 20 of the HIFU device 14. The ultrasound signals detected during changes to the relative distance between probe 18 and probe 20 are shown in FIGS. 3A, 3B, 3C, and 3D.

Figure 3:
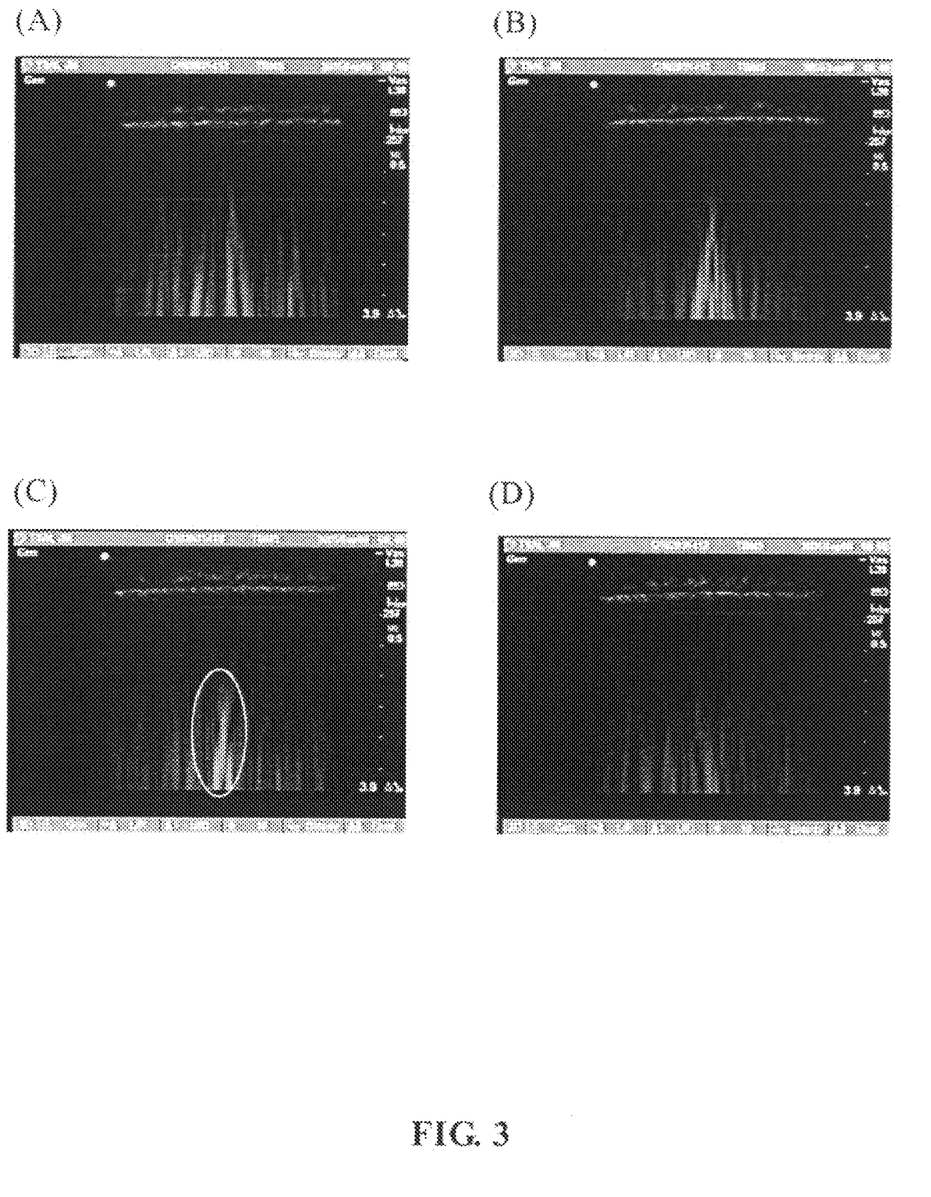
FIGS. 3A, 3B, 3C, and 3D show detected ultrasound signals in purified water as detecting medium during changing the relative distance between a probe of a diagnostic ultrasound device and a probe of a HIFU device (the relative distance is 1.5 cm in FIG. 3A; 3.0 cm in FIG. 3B; 5.0 cm in FIG. 3C; and 7.0 cm in FIG. 3D, respectively)

Referring to FIGS. 3A, 3B, 3C, and 3D, the geometric axis 22 of the probe 18 of the diagnostic ultrasound device 12 and the geometric axis 24 of the probe 20 of the HIFU device 14 are intersected to define an intersection point. The distance between the two probes 18 and 20 is set at 1.5 cm, 3.0 cm, 5.0 cm, and 7.0 cm respectively while ultrasound signals detected according to the above distance are shown in FIGS. 3A, 3B, 3C, and 3D, respectively. As shown in FIG. 3C, when the distance between the two probes 18 and 20 is 5.0 cm, the intersection point is close to the focus location (the predetermined ablating point) of the HIFU device 14 so that FIG. 3C shows an obvious intensive interference signal in the marked region.

Figure 4:
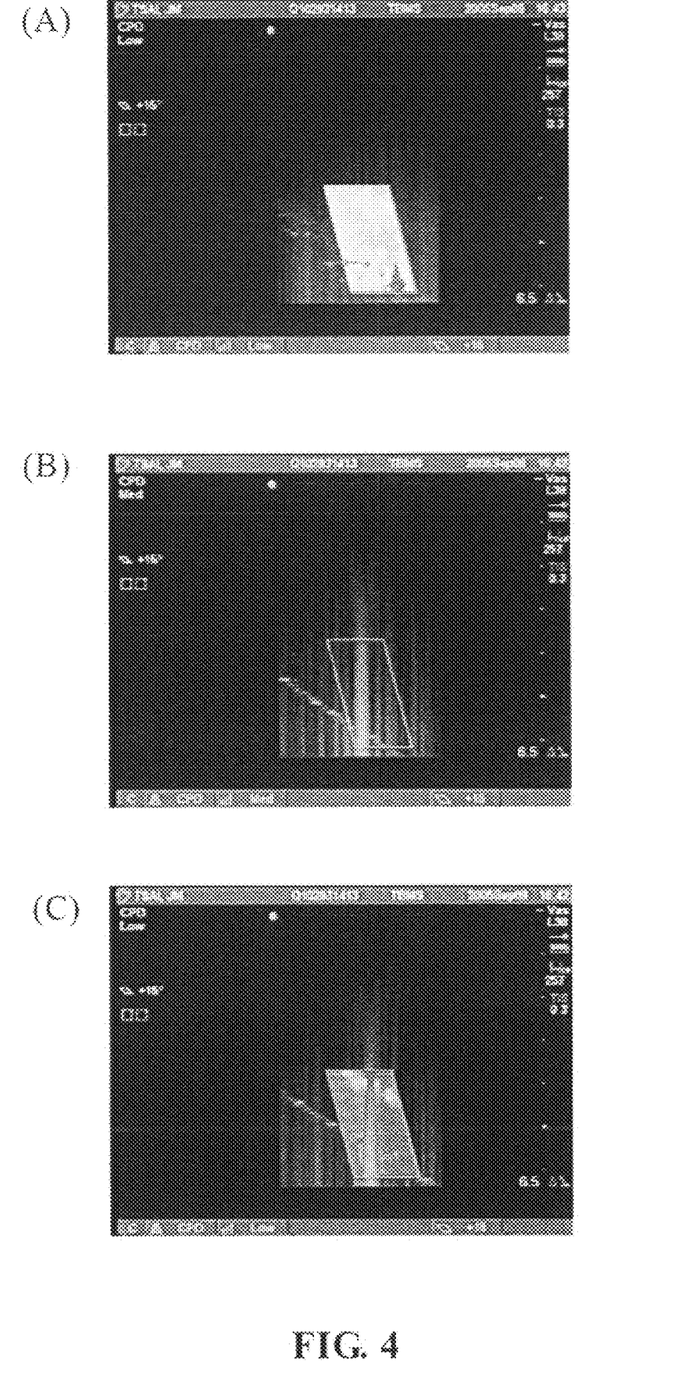
FIGS. 4A, 4B, and 4C are images of interference signals under a B mode or a Doppler mode of the diagnostic ultrasound device according to the preferred embodiment of the present invention (FIG. 4A shows the image of non-intensive interference signals under the Doppler mode.

Referring now to FIGS. 4A, 4B, and 4C, images of interference signals which are changed from a B mode to a Doppler mode of the diagnostic ultrasound device 12 according to the preferred embodiment of the present invention are shown (FIG. 4A shows non-intensive interference signals under the Doppler mode; FIG. 4B shows intensive interference signals under the B mode; and FIG. 4C shows intensive interference signals under the Doppler mode). In FIG. 4A, if the observation plane of the diagnostic ultrasound device 12 is not intersected to the focus of the HIFU device 14 on the geometric axis 24, there will be no obvious interference signals detected. In FIGS. 4B and 4C, if the observation plane of the diagnostic ultrasound device 12 is intersected to the focus of the HIFU device 14 on the geometric axis 24, there will be obvious interference signals detected.

Example 2

Figure 5:
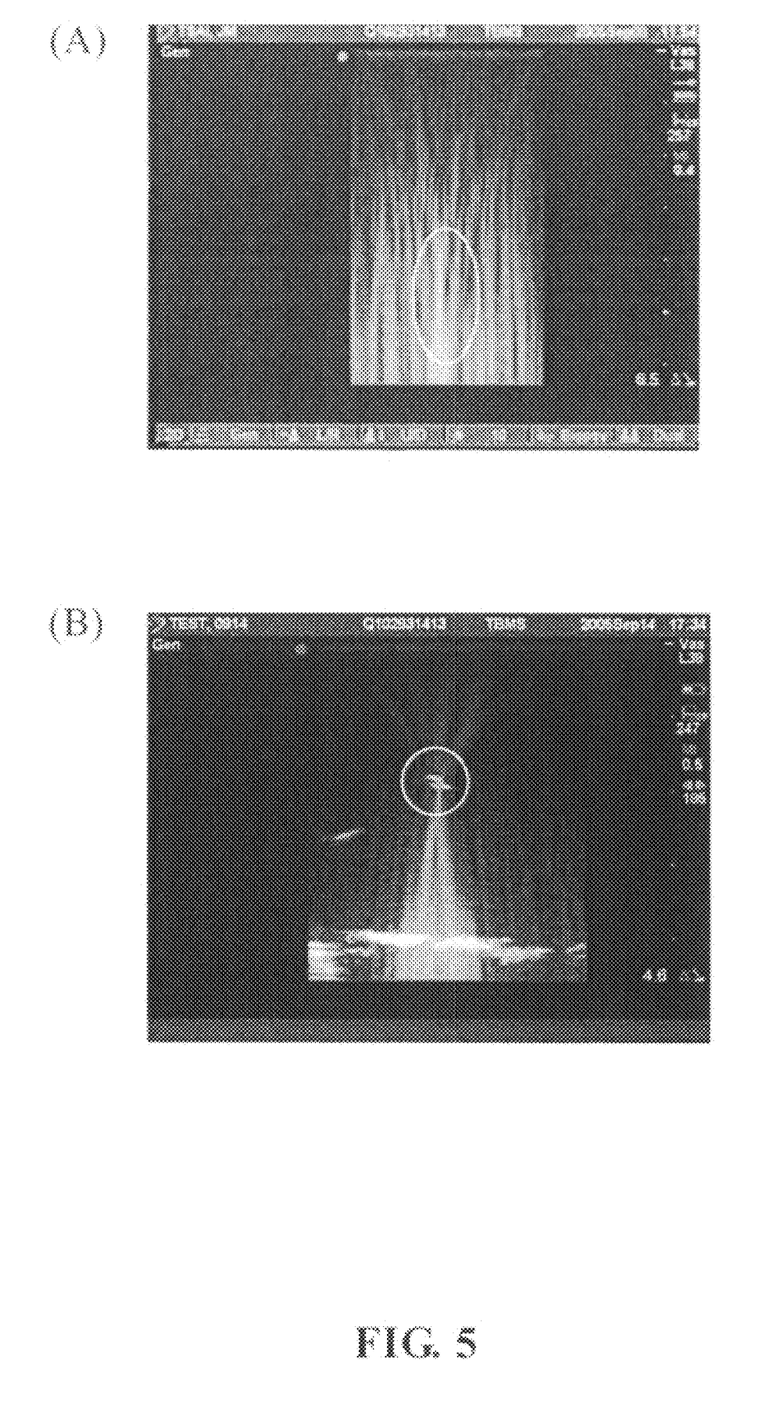
FIGS. 5A and 5B show intensive ultrasound signals detected in an agar medium or a phantom as detecting medium according to the preferred embodiment of the present invention (agar in FIG. 5A; and phantom in FIG. 5B)

Referring now to FIG. 5A, intensive ultrasound signals detected by the non-invasive positioning system 10 in a medium selected from agar to substitute purified water in Example 1 according to the preferred embodiment of the present invention.

Referring now to FIG. 5B, intensive ultrasound signals detected by the non-invasive positioning system 10 in a sample called "phantom" to substitute agar in Example 2 according to the preferred embodiment of the present invention. The phantom is prepared by mixing 30 ml egg white, 40 ml degas water, 24.8 ml acrylamide, 0.5 ml ammonium persulfate (APS), 9 ml glycerol, and 0.2 ml N,N,N'N'-tetramethylethylenediamine (TEMED). Before detecting signals, the HIFU device 14 is used to output a relatively high power to heat a region of the phantom on a focus location (i.e. the predetermined ablating point) until the region of the phantom is boiled at 100° C. to form bubbles at the region. After this, the non-invasive positioning method of the present invention as described above is used, followed by detecting where the intensive interference signals are, as shown in FIG. 5B. It is shown that the intensive interference signals are concentrated where the bubbles are, i.e. the focus location of the HIFU device 14.

Referring still to FIGS. 5A and 5B, the intensive ultrasound signals in agar or phantom detected by the non-invasive positioning system 10 shows the diagnostic ultrasound signals can increase signal intensity on the intersection point to the focus of HIFU device 14 on the geometric axis 24.

Example 3

Figure 6:
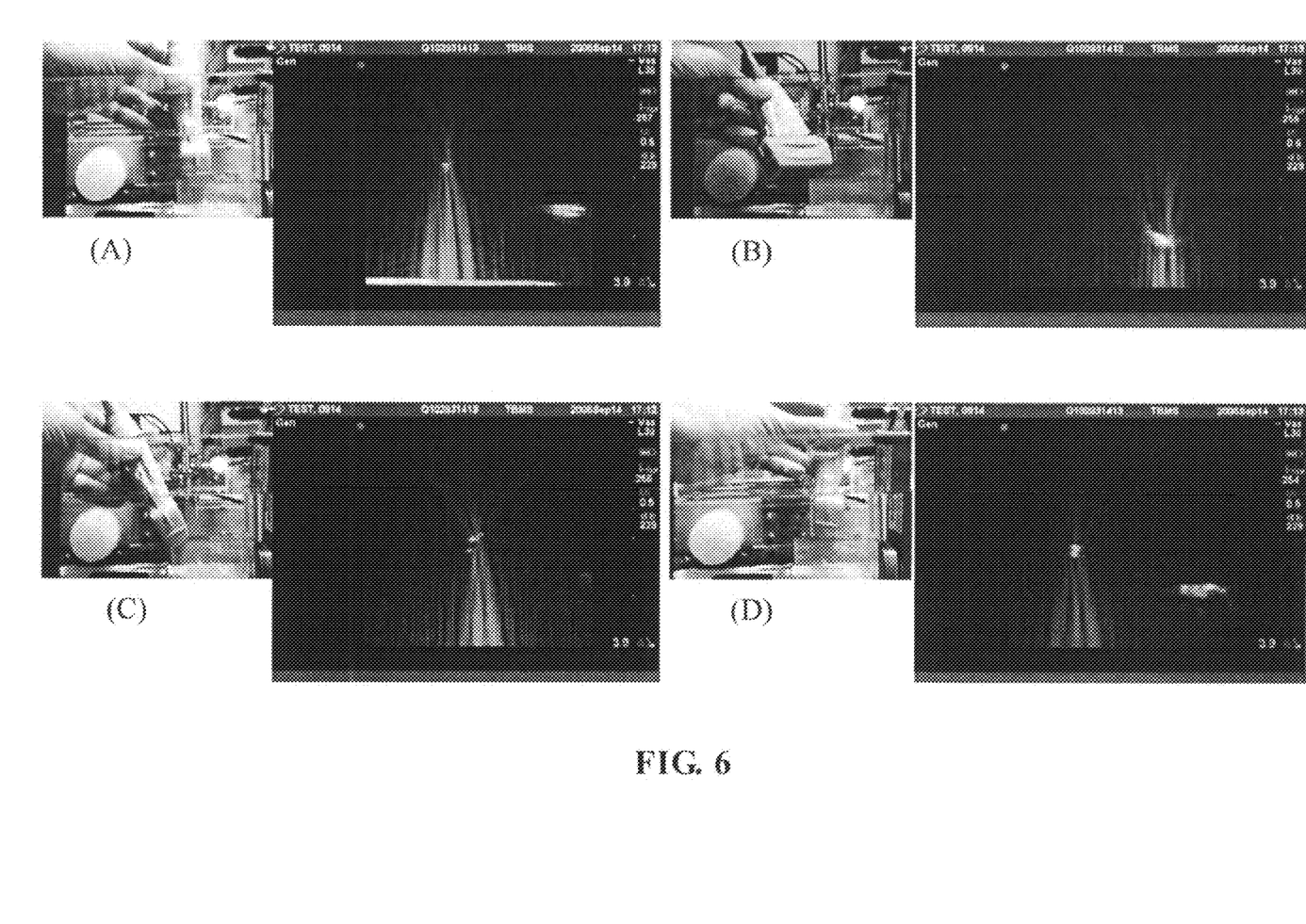
FIGS. 6A, 6B, 6C, and 6D show variations of interference signals detected by the diagnostic ultrasound device under different inclined angles of a probe thereof relative to a probe of the HIFU device according to the preferred embodiment of the present invention (the inclining angle α of the probe is 95 degrees in FIG. 6A; 135 degree with side rotation in FIG. 6B; 160 degrees in FIG. 6C; and 75 degrees in FIG. 6D)

Referring now to FIGS. 6A, 6B, 6C, and 6D, variation of interference signals detected by the diagnostic ultrasound device 12 under different inclining angles of the geometric axis 22 of the probe 18 thereof relative to the geometric axis 24 of the probe 20 of the HIFU device 14 so as to change the inclining angle α of the geometric axes 22, 24, wherein Example 3 uses a similar detection process described in Example 1 under a relatively low power about 0.05 W of the HIFU device 14 and without changing the relative distance between the two probes 18 and 20, and wherein the image results of the diagnostic ultrasound device 12 at the inclining angle α of 95 degrees as shown in FIG. 6A; 135 degree with side rotation as shown in FIG. 6B; 160 degrees as shown in FIG. 6C; and 75 degrees as shown in FIG. 6D.

As a result, whether the geometric axes 22 and 24 are intersected with which includes angle α, the intensive interference signals all can be detected by the diagnostic ultrasound device 12 on the focus location (i.e. the locations of the bubbles).

Example 4

The sample of Example 4 is selected from a commercially available porcine muscle tissue, which is burned in vitro for testing, wherein Example 4 uses a similar detecting process as described in Example 1. In the ablating test, the HIFU device 14 operates at a relatively low power for detecting the focus location thereof (i.e. the predetermined ablating point) by the diagnostic ultrasound device 12, and then the HIFU device 14 operates at a relatively high power for ablating the focus location. After ablating, the porcine muscle tissue is cut and the actual ablating point is detected, as shown in FIGS. 7A and 7B.

Figure 7:
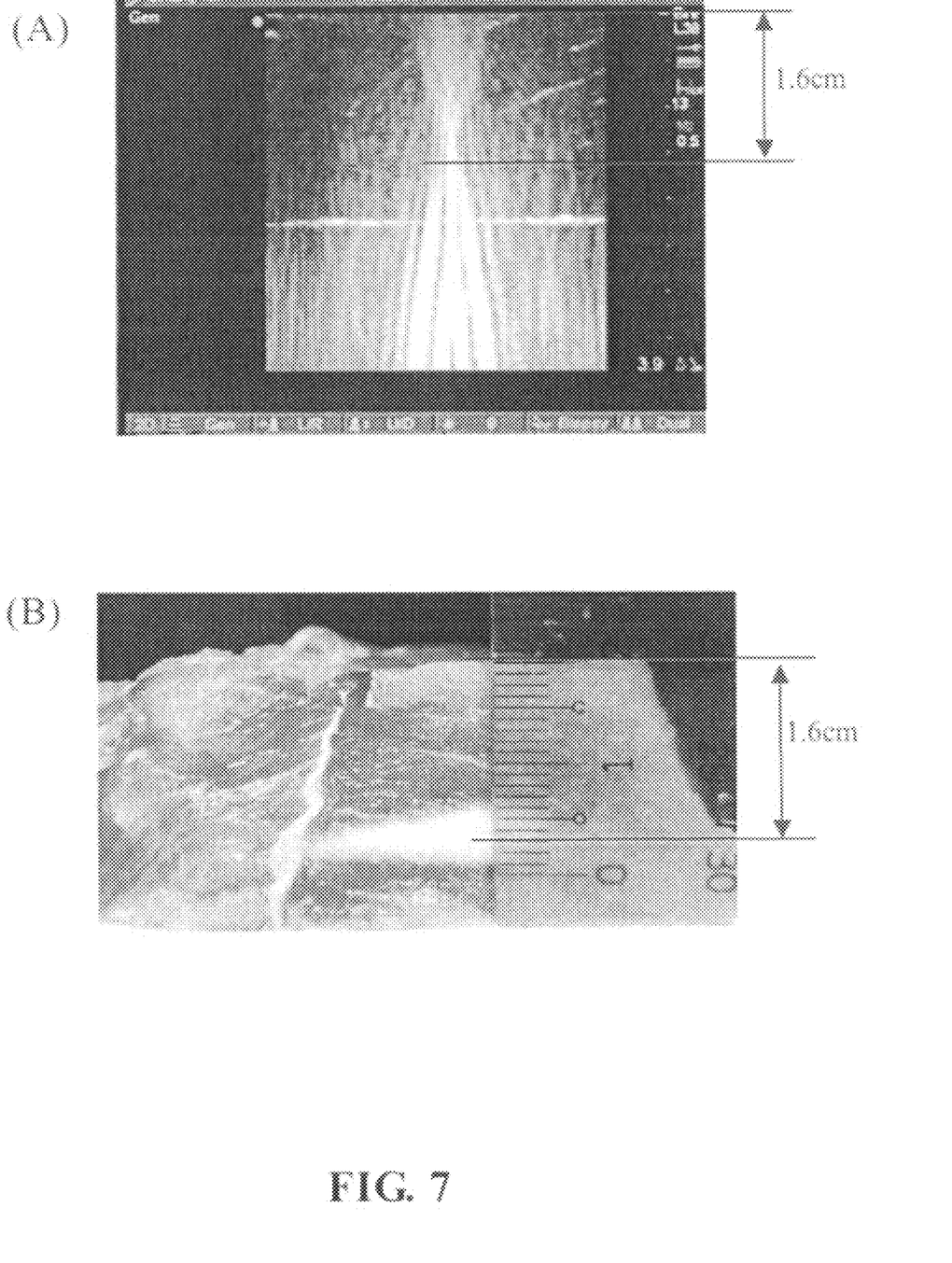
FIGS. 7A and 7B show experimental results from ablating animal muscle tissue via the diagnostic ultrasound device in vitro according to the preferred embodiment of the present invention (FIG. 7A shows a signal image under the B mode of the probe of the diagnostic ultrasound device, and FIG. 7B shows an image of the ablated animal muscle).

Referring now FIGS. 7A and 7B, experimental results by ablating the porcine muscle tissue (or other animal muscle tissue) via the diagnostic ultrasound device 12 in vitro according to the preferred embodiment of the present invention are illustrated, wherein FIG. 7A is a signal image under the B mode of the probe 18 of the diagnostic ultrasound device 12 showing the depth of the focus location (i.e. the predetermined ablating point) is about 1.6 cm within the porcine muscle tissue, and wherein FIG. 7B is an image of the ablated porcine muscle tissue showing the depth of the actual ablating point is really 1.6 cm within the porcine muscle tissue so that the maximal interference convergence (i.e. the predetermined ablating point) is substantially the same as the actual ablating point.

The present invention has been described with a preferred embodiment thereof and it is understood that many changes and modifications in the described embodiment can be carried out without departing from the scope and the spirit of the invention that is intended to be limited only by the appended claims.

What is claimed is:

1. A positioning method for the focus location of a high-intensity focused ultrasound (HIFU) device in vivo, comprising steps of:
    (i) scanning and estimating the location and size of a tumor in vivo using a diagnostic ultrasound device;
    (ii) operating the HIFU device at a relatively low power to align the ultrasound provided thereby with the location of the tumor tissue detected in step (i);
    (iii) adjusting the scanning angle of the diagnostic ultrasound device until maximal interference convergence is observed on the ultrasounds intersection provided respectively from the diagnostic ultrasound device and the HIFU device, wherein the inclining angle defined between geometric axes of the respective probes of the diagnostic ultrasound device and the HIFU device has a range from 85 to 160 degrees; and
    (iv) determining the focus of the HIFU device by locating where the maximal interference convergence is observed using the diagnostic ultrasound device.

2. The positioning method for the focus location of the high-intensity focused ultrasound (HIFU) in vivo as claimed in claim 1, wherein after step (iii), further comprises a step of: ablating the tumor tissue by operating HIFU at a relatively high power to remove the tumor tissue.

3. The positioning method for the focus location of the high-intensity focused ultrasound (HIFU) in vivo as claimed in claim 2, wherein the relatively high power has a range from 30 W to 60 W (electrical power).

4. The positioning method for locating the focus of the high-intensity focused ultrasound (HIFU) in vivo as claimed in claim 1, wherein the relatively low power of step (ii) is from 0.01 W to 5 W (electrical power).

\* \* \* \* \*